United States Patent
Ildstad et al.

(10) Patent No.: US 9,678,062 B2
(45) Date of Patent: Jun. 13, 2017

(54) METHODS AND COMPOSITIONS FOR EXPANDING CELLS AND IMPROVING ENGRAFTMENT

(71) Applicant: University of Louisville Research Foundation, Inc., Louisville, KY (US)

(72) Inventors: Suzanne T. Ildstad, Prospect, KY (US); Mary Jane Elliott, Brandenburg, KY (US)

(73) Assignee: University of Louisville Research Foundation, Inc., Louisville, KY (US)

(*) Notice: Subject to any disclaimer, the term of this patent is extended or adjusted under 35 U.S.C. 154(b) by 0 days.

(21) Appl. No.: 14/346,505

(22) PCT Filed: Sep. 21, 2012

(86) PCT No.: PCT/US2012/056575
§ 371 (c)(1),
(2) Date: Mar. 21, 2014

(87) PCT Pub. No.: WO2013/044029
PCT Pub. Date: Mar. 28, 2013

(65) Prior Publication Data
US 2014/0234843 A1    Aug. 21, 2014

Related U.S. Application Data

(60) Provisional application No. 61/538,633, filed on Sep. 23, 2011.

(51) Int. Cl.
*C12N 5/00*    (2006.01)
*G01N 33/50*    (2006.01)
*C12N 5/0784*    (2010.01)

(52) U.S. Cl.
CPC ....... *G01N 33/5073* (2013.01); *C12N 5/0639* (2013.01); *G01N 33/5029* (2013.01); *C12N 2501/998* (2013.01); *C12N 2502/1171* (2013.01)

(58) Field of Classification Search
None
See application file for complete search history.

(56) References Cited

U.S. PATENT DOCUMENTS

| | | | |
|---|---|---|---|
| 7,429,376 B2 | 9/2008 | Ildstad et al. | |
| 7,985,887 B2 | 7/2011 | Cox, III et al. | |
| 2006/0234294 A1* | 10/2006 | Fukui et al. | 435/7.1 |
| 2010/0173327 A1 | 7/2010 | Fukui et al. | |
| 2011/0110909 A1 | 5/2011 | Ildstad et al. | |

FOREIGN PATENT DOCUMENTS

| | | |
|---|---|---|
| WO | WO84/03564 | 9/1984 |
| WO | WO91/18980 | 12/1991 |
| WO | WO93/06121 | 4/1993 |
| WO | WO94/08051 | 4/1994 |
| WO | WO95/12608 | 5/1995 |
| WO | WO95/30642 | 11/1995 |
| WO | WO95/35503 | 12/1995 |

OTHER PUBLICATIONS

Fukui et al. Nat 2001;412:826-31.*
Kunisaki et al. J Immunol 2006;176:4640-5.*
Nishihara et al. Biochem Biophys Res Comm 2002;716-20.*
Kikuchi et al. Biochem Biophys Res Comm 2008;367:90-6.*
Wikipedia, Lymphpoiesis, last modified Dec. 2014.*
International Search Report and Written Opinion in International Application No. PCT/US2012/056575, mailed Feb. 28, 2013, 11 pages.
International Preliminary Report on Patentability in International Application No. PCT/US2012/056575, issued Mar. 25, 2014, 7 pages.
Colson et al., "Facilitating cells: novel promoters of stem cell alloengraftment and donor-specific transplantation tolerance in the absence of GVHD," Crit. Rev. Oncol. Hematol., 2007, 61(1):26-43.
Fugier-Vivier et al., "Plasmacytoid precursor dendritic cells facilitate allogeneic hematopoietic stem cell engraftment," J. Exp. Med., 2005, 201(3):373-83.
GenBank Accession No. AA111941.1, 2006, 2 pages.
GenBank Accession No. BC104900.1, 2006, 4 pages.
GenBank Accession No. BC107416.1, 2006, 3 pages.
GenBank Accession No. BC111940.1, 2006, 3 pages.
GenBank Accession No. NM_004946.2, 2011, 7 pages.
GenBank Accession No. NP_004937.1, 2011, 3 pages.
GenBank Accession No. Q8N392.3, 2011, 4 pages.
GenBank Accession No. Q92608.2, 2011, 7 pages.
Grimes et al., "Graft facilitating cells are derived from hematopoietic stem cells and functionally require CD3, but are distinct from T lymphocytes," Exp. Hematol., 2004, 32(10):946-54.
Huang et al., "Plasmacytoid precursor dendritic cells from NOD mice exhibit impaired function: are they a component of diabetes pathogenesis?" Diabetes, 2008, 57:2360-70.
Ildstad et al., "Is durable macrochimerism key to achieving clinical transplantation tolerance?" Curr. Opin. Organ Transplant, 2011, 16(4):343-4.
Kaufman et al., "Phenotypic characterization of a novel bone marrow-derived cell that facilitates engraftment of allogeneic bone marrow stem cells," Blood, 1994, 84(8):2436-46.
Kunisaki et al., "Dock2 is a Rac activator that regulates motility and polarity during neutrophil chemotaxis," J Cell Biol., Aug. 2006, 174(5):647-652.
Maeda et al., "ARHGAP18, a GTPase-activating protein for RhoA, controls cell shape, spreading, and motility," Molecular Biol Cell, Aug. 2011, 22(20):3840-3852.
Rezzoug et al., "TNF-alpha is critical to facilitate hemopoietic stem cell engraftment and function," J. Immunol., 2008, 180(1):49-57.

(Continued)

*Primary Examiner* — Janice Li
(74) *Attorney, Agent, or Firm* — Fish & Richardson P.C.

(57) ABSTRACT

Methods of expanding FCs or stem cells are provided herein, as are methods of screening for compounds that increase expression of DOCK2 or decrease expression of Arhgap18, either of which improves engraftment.

6 Claims, 12 Drawing Sheets

(56) References Cited

OTHER PUBLICATIONS

Garcia-Bernal et al., "Dock2 is required for Chemokine-Promoted Human T Lymphocyte Adhesion Under Shear Stress Mediated by the Integrin α4β1," J Immunol., 2006, 177:5215-5225.

Jiang et al., "Deletion of DOCK2, a regulator of the actin cytoskeleton in lymphocytes, suppresses cardiac allograft rejection," JEM, 2005, 202:1121-1130.

Wang et al., "Dock2 regulates, cell proliferation through Rac and ERK activation in B cell lymphoma," Biochem Biophys Res Comm., 2010, 395(1):111-115.

Partial Supplementary European Search Report in Application No. 12833937.1 dated Apr. 1, 2015, 9 pages.

Gotoh et al., "Differential requirement for DOCK2 in migration of plasmacytoid dendritic cells versus myeloid dendritic cells," Blood, 2008, 111(6):2973-2976.

Sanui et al., "DOCK2 is essential for antigen-induced translocation of TCR and lipid rafts, but not PKC-THETA and LFA-1, in T Cells," Immunity, 2003, 19(10):119-129.

Wen et al., "DOCK2 is critical for DC8<+>TCR<−> graft facilitating cells to enhance engraftment of hematopoietic stem and progenitor cells," Stem Cells, 2014, 32(10):2732-2743.

\* cited by examiner

A

B

A

B

METHODS AND COMPOSITIONS FOR EXPANDING CELLS AND IMPROVING ENGRAFTMENT

CROSS-REFERENCE TO RELATED APPLICATION

This application is a National Stage Application under 35 U.S.C. §371 and claims the benefit of International Application No. PCT/US2012/056575, filed Sep. 21, 2012, which claims priority under 35 U.S.C. 119(e) to U.S. Application Ser. No. 61/538,633, filed on Sep. 23, 2011, entitled METHODS AND COMPOSITIONS FOR EXPANDING CELLS AND IMPROVING ENGRAFTMENT, the disclosures of which are incorporated by reference in their entirety.

FEDERAL FUNDING LEGEND

This invention was made with Government support under W81XWH-10-1-0688 awarded by the U.S. Department of Defense. The Government has certain rights in this invention.

TECHNICAL FIELD

This disclosure generally relates to methods of expanding facilitating cells (FCs) or stem cells and methods of improving engraftment.

BACKGROUND

CD8+/TCR-graft facilitating cells (FCs) enhance engraftment of hematopoietic stem cells (HSCs) in both MHC-disparate and syngeneic recipients. FCs are a heterogeneous population of cells, with a predominant sub-population resembling plasmacytoid precursor dendritic cells (p-preDCs). FCs enhance clonogenicity of HSCs in vitro, induce antigen-specific regulatory T cells in vivo, and mediate prevention of GVHD.

SUMMARY

In one aspect, a method of expanding FCs is provided. Such a method includes the step of contacting the FCs with DOCK2 polypeptides. In another aspect, a method of expanding stem cells (IPCs; HSCs; cord blood, etc.) is provided. Such a method includes the step of contacting the stem cells with DOCK2 polypeptides. In still another aspect, a method of improving engraftment of donor HSCs in the recipient is provided. Such a method includes the step of transplanting a therapeutic cellular composition into a patient. According to this disclosure, the therapeutic cellular composition is expanded and/or transplanted in the presence of DOCK2 polypeptides. In yet another aspect, a method of up-regulating expression of DOCK2 in FCs is provided. Such a method includes the step of contacting FCs with a zinc-finger nucleic acid that up-regulates the expression of DOCK2. In some embodiments, the DOCK2 polypeptides are human DOCK2 polypeptides. In some embodiments, the DOCK2 polypeptides are recombinant DOCK2 fusion polypeptides.

In one aspect, a method of screening for a compound that increases the expression of DOCK2 is provided. Such a method includes the steps of contacting DOCK2-expressing cells with a test compound; and determining the amount of DOCK2 RNA or protein. Typically, an increase in DOCK2 RNA or protein in the presence of the test compound compared with the amount of DOCK2 RNA or protein in a cell not contacted with the test compound is indicative of a compound that increases the expression of DOCK2. In some embodiments, the DOCK2-expressing cells are DOCK2-expressing hematopoietic cells. In some embodiments, the DOC2-expressing hematopoietic cells are FCs. In some embodiments, the DOCK2-expressing cells are cells that express a recombinant DOCK2 nucleic acid.

In another aspect, a method of screening for a compound that decreases the expression of Arhgap18 is provided. Such a method includes the steps of contacting Arhgap18-expressing cells with a test compound; and determining the amount of Arhgap18 RNA or protein. Typically, a decrease in Arhgap18 RNA or protein in the presence of the test compound compared with the amount of Arhgap18 RNA or protein in an Arhgap18-expressing cell not contacted with the test compound is indicative of a compound that decreases the expression of Arhgap18. In some embodiments, the Arhgap18-expressing cells are Arhgap18-expressing hematopoietic cells. In some embodiments, the Arhgap18-expressing hematopoietic cells are FCs. In some embodiments, the Arhgap18-expressing cells are cells that express a recombinant Arhgap18 nucleic acid.

Representative methods of determining the amount of RNA is Northern blot. Representative methods of determining the amount of protein is ELISA.

In another embodiment, a method of screening for a compound that increases the migration of FCs toward chemokines is provided. Such a method includes the steps of contacting FCs with a test compound, wherein the FCs are cultured in the vicinity of a chemokine; and determining whether or not there is an increase in the migration of FCs toward the chemokine compared to the migration of FCs that have not been contacted with the test compound, wherein an increase in migration of the FCs toward the chemokine in the presence of the test compound compared to the migration of the FCs toward the chemokine in the absence of the test compound indicates a compound that increases the migration of FCs toward chemokines. In some embodiments, the chemokine is SDF-1. In some embodiments, the method uses trans-well migration.

In some embodiments of the methods described herein, the FCs are purified. In some embodiments of the methods described herein, the compound is selected from the group consisting of small molecules, polypeptides, synthetic compounds, naturally-occurring compounds, antibodies, antigen-binding fragment, and antigens.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DETAILED DESCRIPTION

Figure 1:
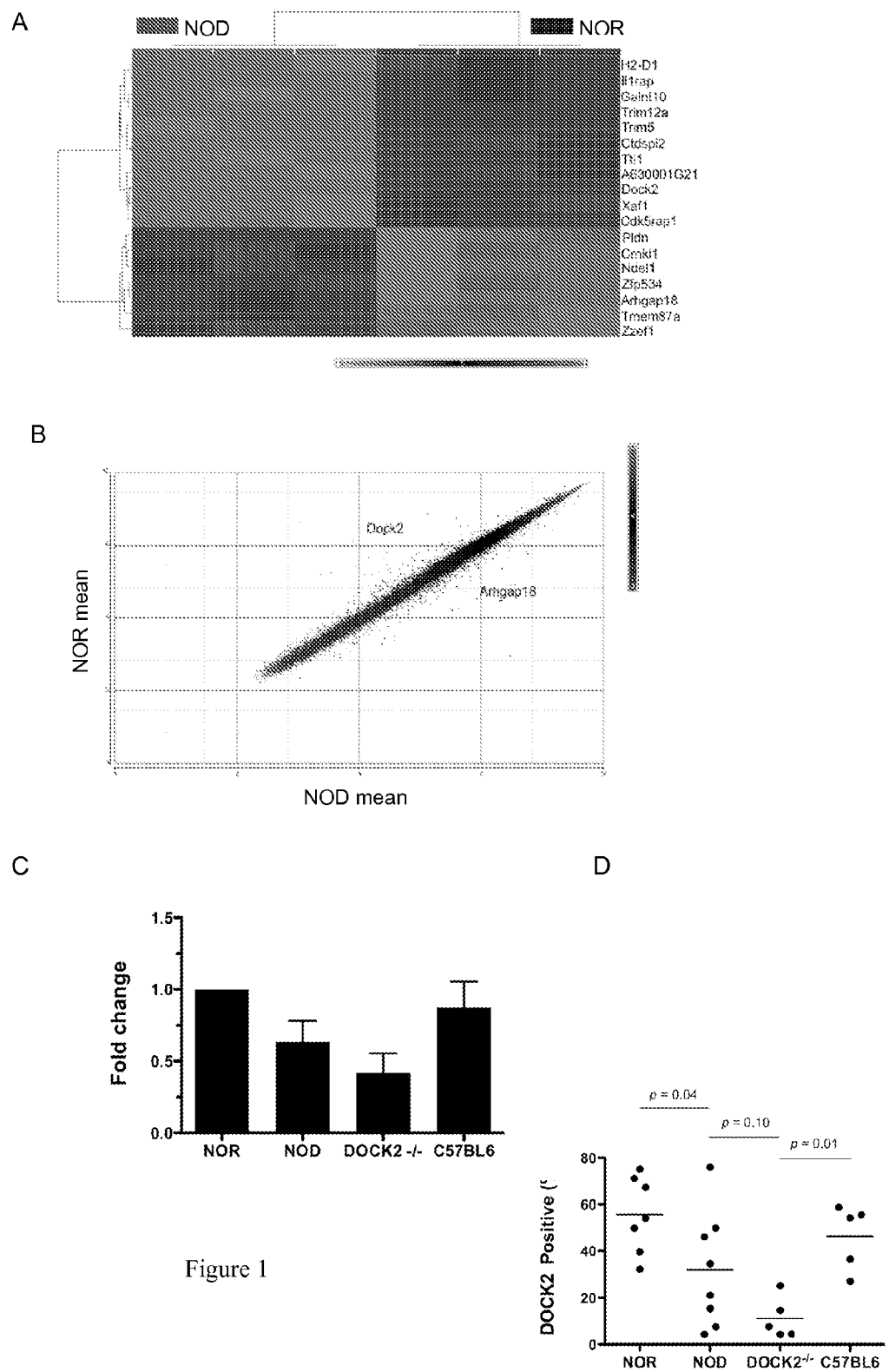
FIG. 1 shows the gene expression profile based on microarray analysis. (A) Hierarchical clustering of differentially expressed genes. The top 18 most significant differentially expressed genes were revealed by false discovery rate (FDR) control analysis with a cut-off value at level 1.99952$^{e-0.05}$. Each lane represents the expression profile of one batch of FC sample. The first 3 lanes show the expression profiles of FC isolated from NOD mice and the last 3 lanes display FC from NOR mice. (B) Scatter plot of the mean log 2 based signals for each group, NOR FC and NOD FC. (C) Quantitative real-time RT-PCR (qRT-PCR) analysis of Dock2 RNA levels in FC from the indicated mouse strains. Data were representative of five individual experiments and values represented the fold changes normalized with NOR mouse strain. In each experiment, FCs were sorted from bone marrow cells harvested from three animals per strain. qRT-PCR was performed in triplicate for each sample (n=5 for each group). (D) High content immunofluorescence image analysis of DOCK2 protein levels in the indicated mouse strains. Data were shown by dot plot. Each dot represents a single mouse. The DOCK2$^{-/-}$ mice were used as a negative control and wild-type B6 mice as a positive control in both assays.

Methods of expanding FCs or stem cells are described herein, as are methods of screening for compounds that increase expression of DOCK2 or decrease expression of Arhgap18. As demonstrated herein, contacting FCs or stem cells with DOCK2 or increasing the expression of DOCK2 in FCs or HSCs improves engraftment of donor HSCs in a recipient. Likewise, decreasing the expression of Arhgap18 in FCs or stem cells also should improve engraftment.

Methods of Expanding Stem Cells

Methods of expanding FCs or stem cells are provided, and include the step of contacting the FCs or stem cells with DOCK2 polypeptides. FCs are described in a number of references including, for example, US 2011/0110909 and Ildstad et al., 2011, *Curr. Opin. Organ Transplant*, 16:343-4 and Colson et al., 2007, *Crit. Rev. Oncol. Hematol.*, 61:26-43. As used herein, stem cells refer to any type of cell that has the ability for self-renewal and also, under certain conditions, can differentiate into tissue- or organ-specific cells. Stem cells include, without limitation, embryonic stem cells, adult stem cells, and induced pluripotent stem cells (iPSCs). Stem cells can be purified, or stem cells can be in a biological sample such as, for example, bone marrow or cord blood. As used herein, "expanding" refers to increasing the number of cells in the culture by at least 2-fold (e.g., 5-fold, 10-fold, 20-fold, 50-fold, or 100-fold increase).

Methods of improving engraftment of donor HSCs in a recipient are also provided. This method utilizes the therapeutic cellular composition described in US 2011/0110909, which includes HSCs, FCs and alpha beta TCR+ T cells. According to the methods described herein, the cells in such a therapeutic cellular composition (e.g., the FCs, the HSCs) can be expanded in the presence of DOCK2 polypeptides. Additionally or alternatively, such a therapeutic cellular composition can be transplanted into the patient in the presence of DOCK2 polypeptides.

DOCK2 (dedicator of cytokinesis 2) polypeptides are member of the *Caenorhabditis elegans* Ced-5, the mammalian DOCK180 and the *Drosophila melanogaster* myoblast city (CDM) families of guanine nucleotide exchange factors. The human DOCK2 protein is 1842 amino acids and has a molecular weight of 210 kDa. DOCK2 is specifically expressed in hematopoietic cells, and is required for lymphocyte chemotaxis. DOCK2 activates the Rac1 and Rac2 small GTPases, presumably by functioning as a guanine nucleotide exchange factor (GEF). Nucleic acid sequences encoding human DOCK2 polypeptides can be found for example, in GenBank Accession Nos. NM_004946.2 and BC104900.1, while the sequence of the encoded human DOCK2 polypeptides can be found, for example, in GenBank Accession No. NP_004937.1 and Q92608.2.

In addition, methods of up-regulating expression of DOCK2 in FCs are provided, and include the step of contacting FCs with a zinc-finger-containing polypeptide that up-regulates the expression of DOCK2. Zinc-finger-containing polypeptides are well-known in the art as DNA-binding proteins (e.g., transcription factor) and can be engineered to up-regulate or down-regulate expression of a gene. See, for example, U.S. Pat. No. 7,985,887; as well as Sander et al., 2007, *Nuc. Acid Res.*, 35:W599-605; Sander et al., 2010, Nuc. Acid Res., 38:W462-8; and Maeder et al., 2008, *Mol. Cell.*, 31:294-301.

Screening for Compounds that Improve Engraftment of HSCs

Based on the experimental results described herein, methods of screening for compounds that increase engraftment of hematopoietic stem cells (HSCs) are provided. For example, methods are described in which compounds are screened for those that increase the expression of DOCK2 or that decrease the expression of Arhgap18 in DOCK2- or Arhgap18-expressing cells, respectively. Methods also are described in which compounds are screened to identify those that increase the migration of FCs toward chemokines.

DOCK2 polypeptides are described above. Arhgap18 polypeptides belong to a family of Rho GTPase-activating proteins that modulate cell signaling. Arhgap18 activates GTPases by converting them to an inactive GDP-bound state. Nucleic acid sequences encoding Arhgap18 polypeptides can be found, for example, at GenBank Accession No. BC111940.1 and BC107416.1, and the sequence of Arhgap18 polypeptides can be found, for example, at GenBank Accession No. Q8N392.3 and AAI11941.1.

The screening methods disclosed herein typically include contacting a DOCK2- or Arhgap18-expressing cell with a test compound. For use in the screening methods herein, a DOCK2- or Arhgap18-expressing cell can be a hematopoietic cell that naturally expresses DOCK2 or Arhgap18 (e.g., FCs) or a recombinant cell that is genetically engineered to express a nucleic acid encoding a DOCK2 or Arhgap18 polypeptide. It would be understood by those skilled in the art that the nucleic acid encoding DOCK2 or Arhgap18 polypeptides can be endogenous (e.g., native) to the DOCK2- or Arhgap18-expressing cell, or the nucleic acid encoding DOCK2 or Arhgap18 polypeptides can be exogenous (e.g., heterologous) to the DOCK2- or Arhgap18-expressing cell.

The screening methods disclosed herein include measuring the amount of the polypeptide in the presence and absence of the test compound. As indicated herein, an increase in the amount of the DOCK2 polypeptide in the presence of the test compound compared to the amount of the DOCK2 polypeptide in the absence of the test compound identifies a compound that expands FCs or stem cells. Similarly, a decrease in the amount of the Arhgap18 polypeptide in the presence of the test compound compared to the amount of the Arhgap18 polypeptide in the absence of the test compound identifies a compound that expands FCs or stem cells. It would be understood by those skilled in the art that expanding FCs or stem cells (e.g., HSCs) prior to or during transplantation results in improved engraftment.

Many of the methods described herein for screening compounds are highly amenable to automation and high throughput. See, for example, WO 84/03564 for a description of high throughput screening of compounds, and Farrelly et al. (2001, *Analytical Biochemistry*, 293:269-276) for a description of high throughput methods to screen for compounds that affect protein binding and transcriptional activation via protein binding.

Polypeptides, Nucleic Acids Encoding the Polypeptides, and Recombinant Cells

With respect to polypeptides, the term "purified" refers to a polypeptide that has been separated or purified from cellular components that naturally accompany it. Typically, the polypeptide is considered "purified" when it is at least 70% (e.g., at least 75%, 80%, 85%, 90%, 95%, or 99%) by dry weight, free from the proteins and naturally occurring molecules with which it is naturally associated. Since a polypeptide that is chemically synthesized is, by nature, separated from the components that naturally accompany it, a synthetic polypeptide is "purified".

Polypeptides can be purified from natural sources (e.g., cell lysates) by known methods such as DEAE ion exchange, gel filtration, and hydroxyapatite chromatography. In addition, a purified polypeptide can be obtained by chemical synthesis. The extent of purity of a polypeptide can be measured using any appropriate method, e.g., column chromatography, polyacrylamide gel electrophoresis, or HPLC analysis. As described in more detail below, a purified polypeptide also can be obtained by expressing a nucleic acid encoding the polypeptide.

The above-described polypeptides can be encoded by the respective nucleic acid sequences associated with the above-referenced GenBank Accession Numbers. Those of skill in the art would understand, however, that, based on the degenerate code, a number of different nucleic acids can be designed that encode the same polypeptide. The term "nucleic acid" can refer to DNA molecules and RNA molecules as well as analogs of the DNA or RNA molecule generated using nucleotide analogs. A nucleic acid as described herein can be single-stranded or double-stranded, which generally is dependent upon its intended use.

As used herein, an "isolated" nucleic acid is a nucleic acid that is separated from other nucleic acids that are usually associated with the isolated nucleic acid. Thus, an "isolated" nucleic acid includes, without limitation, a nucleic acid that is free of sequences that naturally flank one or both ends of the nucleic acid in the genome of the organism from which the isolated nucleic acid is derived (e.g., a cDNA or genomic DNA fragment produced by PCR or restriction endonuclease digestion). In addition, an isolated nucleic acid molecule can include an engineered nucleic acid such as a recombinant or a synthetic nucleic acid. A nucleic acid existing among hundreds to millions of other nucleic acid molecules within, for example, a nucleic acid library (e.g., a cDNA, or genomic library) or a portion of a gel (e.g., agarose, or polyacrylamide) containing restriction-digested genomic DNA is not to be considered an isolated nucleic acid.

Isolated nucleic acids can be obtained using techniques routine in the art. For example, isolated nucleic acids can be obtained using any method including, without limitation, recombinant nucleic acid technology, and/or the polymerase chain reaction (PCR). General PCR techniques are described, for example in *PCR Primer: A Laboratory Manual*, 1995, Dieffenbach & Dveksler, Eds., Cold Spring Harbor Laboratory Press. Recombinant nucleic acid techniques include, for example, restriction enzyme digestion and ligation, which can be used to isolate a nucleic acid. Isolated nucleic acids also can be chemically synthesized, either as a single nucleic acid or as a series of oligonucleotides.

In addition to naturally-occurring sequences, the skilled artisan will further appreciate that changes can be introduced into a nucleic acid using methods routine in the art, thereby leading to changes in the amino acid sequence of the encoded polypeptide. For example, changes can be introduced into nucleic acid coding sequences leading to conservative amino acid substitutions at one or more amino acid residues. A "conservative amino acid substitution" is one in which one amino acid residue is replaced with a different amino acid residue having similar characteristics (see, for example, Dayhoff et al., 1978, in *Atlas of Protein Sequence and Structure*, 5(3):345-352).

A nucleic acid or polypeptide sequence can be compared to another sequence and described in terms of its percent sequence identity. In calculating percent sequence identity, two sequences are aligned and the number of identical matches of nucleotides or amino acid residues between the two sequences is determined. The number of identical matches is divided by the length of the aligned region (i.e., the number of aligned nucleotides or amino acid residues) and multiplied by 100 to arrive at a percent sequence identity value. It will be appreciated that the length of the aligned region can be a portion of one or both sequences up to the full-length size of the shortest sequence. It will be appreciated that a single sequence can align differently with other sequences and hence, can have different percent sequence identity values over each aligned region. It is noted that the percent identity value is usually rounded to the nearest integer.

The alignment of two or more sequences to determine percent sequence identity is performed using the algorithm described by Altschul et al. (1997, *Nucleic Acids Res.*, 25:3389-3402) as incorporated into BLAST (basic local alignment search tool) programs, available at ncbi.nlm.nih.gov on the World Wide Web. BLAST searches can be performed to determine percent sequence identity between a first nucleic acid and any other sequence or portion thereof aligned using the Altschul et al. algorithm. BLASTN is the program used to align and compare the identity between nucleic acid sequences, while BLASTP is the program used to align and compare the identity between amino acid sequences. When utilizing BLAST programs to calculate the percent identity between a sequence of the invention and another sequence, the default parameters of the respective programs are used.

Constructs containing such nucleic acids also are provided. Constructs, including expression vectors, are commercially available and/or can be produced by recombinant DNA technology methods routine in the art. A construct containing nucleic acid encoding one or more polypeptides also can have elements necessary for expression operably linked to such a nucleic acid, and further can include sequences such as those encoding a selectable marker (e.g., an antibiotic resistance gene), and/or those that can be used in purification of a polypeptide (e.g., 6× His tag). Elements necessary for expression include nucleic acid sequences that direct and regulate expression of coding sequences. One example of an element necessary for expression is a promoter sequence. Elements necessary for expression also can include introns, enhancer sequences, response elements, or inducible elements that modulate expression of a coding sequence. Elements necessary for expression can be of bacterial, yeast, insect, mammalian, or viral origin and vectors can contain a combination of elements from different origins. As used herein, operably linked means that a promoter and/or other regulatory element(s) are positioned in a construct relative to a coding sequence in such a way as to direct or regulate expression of the coding sequence. Many methods for introducing nucleic acids into cells are well known to those skilled in the art and include, without limitation, calcium phosphate precipitation, electroporation, heat shock, lipofection, microinjection, and viral-mediated nucleic acid transfer.

The nucleic acids described herein (e.g., in constructs) can be introduced into cells to thereby generate recombinant cells. The term "recombinant cell" refers not only to the particular cell into which the nucleic acid has been introduced but also to the progeny of such a cell. A recombinant cell can be a prokaryotic cell or a eukaryotic cell. For example, nucleic acids can be expressed in bacterial cells such as *E. coli*, or in insect, yeast or mammalian cells (such as Chinese hamster ovary cells (CHO) or COS cells). Other suitable host cells that can be made recombinant are known to those skilled in the art.

The methods described herein for manipulating nucleic acids in order to express the desired combination of polypeptides require nothing more than standard molecular biology techniques that are well known in the art. Such routine molecular biology techniques are described, for example, in *Molecular Cloning: A Laboratory Manual*, Sambrook et al., Cold Spring Harbor Press (2001); and in *PCR Primer: A Laboratory Manual*, 1995, Dieffenbach & Dveksler, Eds., Cold Spring Harbor Laboratory Press, Cold Spring Harbor, N.Y.

Compounds for Use in the Screening Methods

Any number of different compounds can be screened in the methods described herein. Representative compounds include, for example, small molecules, polypeptides, synthetic compounds, naturally-occurring compounds, antibodies, antigen-binding fragment, or antigens.

Compounds that can be screened in the methods herein can include antibodies. As used herein, the term "antibody" is used in the broadest sense and includes fully assembled antibodies, monoclonal antibodies, polyclonal antibodies, multispecific antibodies (including bispecific antibodies), antibody fragments that can bind an antigen (including, Fab', F'(ab)2, Fv, single chain antibodies, diabodies), and recombinant peptides comprising the foregoing as long as they exhibit the desired biological activity. Multimers or aggregates of intact molecules and/or fragments, including derivatized multimers, aggregates or fragments, are contemplated. Antibodies of any isotype class or subclass, including IgG, IgM, IgD, IgA, and IgE, IgG1, IgG2, IgG3, IgG4, IgA1 and IgA2, or any allotype, also are contemplated.

In addition, compounds used in the screening methods described herein can include nucleic acids (e.g., oligonucleotides) or pharmaceutically acceptable salts thereof. Non-limiting examples include antisense oligonucleotides, triplex oligonucleotides, ribozymes/deoxyribozymes (DNAzymes), small-interfering RNAs/RNAi, short hairpin RNA, aptamers, ribozymes or decoy oligonucleotides.

For example, small molecule libraries (e.g., chemical libraries, natural product libraries) can be obtained from various commercial sources, while other types of libraries (e.g., combinatorially generated nucleic acid or peptide libraries), can be generated using known methods. Simply by way of example, large combinatorial libraries of compounds can be constructed by the encoded synthetic libraries (ESL) methods described in WO 95/12608, WO 93/06121, WO 94/08051, WO 95/35503 and WO 95/30642. Peptide libraries can also be generated by phage display methods (see, e.g., WO 91/18980). Compounds to be screened can also be obtained from governmental or private sources including, e.g., the DIVERSet E library from ChemBridge Corporation (San Diego, Calif.), the National Cancer Institute's (NCI) Natural Product Repository, Bethesda, Md., the NCI Open Synthetic Compound Collection; Bethesda, Md., or NCI's Developmental Therapeutics Program.

Compositions and Pharmaceutical Compositions

A DOCK2 polypeptide or any of the compounds identified in the screening methods described herein can be combined ex vivo with cells (e.g., FCs, HSCs) or a source of cells (e.g., bone marrow, cord blood). An appropriate amount of a DOCK2 polypeptide or a compound identified in one of the screening methods described herein will be dependent upon a number of different factors (e.g., types of cells, number and/or density of cells), and such amounts can be determined using conventional and well known methods. In addition, cells or a source of cells can be contacted ex vivo with a DOCK2 polypeptide or a compound identified in one of the screening methods described herein at any time from collection from a donor to transplantation into a recipient.

Alternatively, any such compounds can be formulated with a pharmaceutically acceptable carrier for delivery to an individual. The particular formulation, will be dependent upon a variety of factors, including route of administration, dosage and dosage interval of a compound the sex, age, and weight of the individual being treated, the severity of the affliction, and the judgment of the individual's physician. As used herein, "pharmaceutically acceptable carrier" is intended to include any and all excipients, solvents, dispersion media, coatings, antibacterial and anti-fungal agents, isotonic and absorption delaying agents, and the like, compatible with administration. The use of such media and agents for pharmaceutically acceptable carriers is well known in the art. Except insofar as any conventional media or agent is incompatible with a compound, use thereof is contemplated.

Pharmaceutically acceptable carriers for delivering compounds are well known in the art. See, for example *Remington: The Science and Practice of Pharmacy*, University of the Sciences in Philadelphia, Ed., 21$^{st}$ Edition, 2005, Lippincott Williams & Wilkins; and *The Pharmacological Basis of Therapeutics*, Goodman and Gilman, Eds., 12$^{th}$ Ed., 2001, McGraw-Hill Co. The type of pharmaceutically acceptable carrier used in a particular formulation can depend on various factors, such as, for example, the physical and chemical properties of the compound, the route of administration, and the manufacturing procedure. Suitable routes of administration include, for example, parenteral administration (e.g., intravenous, intramuscular, subcutaneous), intraperitoneal administration, and oral administration.

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Example 1—Mice 6 to 8-week old C57BL/6J (B6) [H-2$^b$] and B10.BR/SgSnJ (B10.BR) [H-2$^k$] mice were purchased from the Jackson Laboratory. DOCK2$^{-/-}$ mice (B6 background) [H-2$^b$] have been described elsewhere (Fukui et al., 2001, Nature, 412:826-31). DOCK2$^{-/-}$ mice were backcrossed with B6 mice for more than five generations and B6 mice were used as wild-type (WT) controls. DOCK2$^{-/-}$ littermates were obtained by intercrossing male and female DOCK2$^{-/-}$ mice. 6 to 8-week old DOCK2$^{-/-}$ mice were used in this study. Animals were housed under specific pathogen-free conditions in the animal facility at the Institute for Cellular Therapeutics, University of Louisville, and were cared for according to National Institutes of Health animal care guidelines. All experiments were conducted in accordance with the guidelines of Institutional Animal Care and Use Committee at University of Louisville.

Example 2—Sorting of HSC and FC

HSC and FC were isolated from bone marrow cells by multi-parameter, live sterile cell sorting (FACSVantage SE and FACSAria SORP cell sorter, BD Biosciences), as described previously (Fugier-Vivier et al., 2005, J. Exp. Med., 201:373-83; Huang et al., 2008, Diabetes, 57:2360-70; Rezzoug et al., 2008, J. Immunol., 180:49-57). All following monoclonal antibodies for sorting were purchased from BD Bioscience: stem cell antigen-1 (Sca-1) phycoerythrin (PE), CD117 (c-Kit) allophycocyanin (APC), CD8α fluorescein isothiocyanate (FITC), CD11b FITC, B220 FITC, Gr-1 FITC, TCRαβ FITC, TCRγδ FITC and CD8α PE. HSC were sorted for c-Kit$^+$/Sca-1$^+$/Lin$^-$ (KSL) expression; FC were sorted for CD8α$^+$/TCRαβ$^-$/TCRγδ$^-$ expression. Sorted cells with post-sorting purity ranging from 90-98% were used for experiments.

Example 3—Gene Microarray $3 \times 10^5$ FC were sorted from bone marrow cells collected from 6-8 week old NOD or NOR mice. Total RNA was isolated using the Arcturus® PicoPure® RNA Isolation Kit (Applied Biosystems). Samples for microarray analysis were processed in triplicates. Total RNA was labeled using a 2-cycle labeling kit (Affymetrix) according to the manufacturer's instructions. The labeled RNA was hybridized to GeneChip® Mouse Genome 430 2.0 arrays (Affymetrix). Arrays were washed and stained using an Affymetrix FS450 Fluidics Station and scanned on an Affymetrix GeneChip Scanner 3000 7G. The resulting files were imported into Partek Genomics Suite for analysis. Each GeneChip contained over 45,000 probe sets and therefore a total of 270,000 expression data points were generated from the six arrays. Principle component analysis (PCA) was first performed to examine correlations among the data produced from different arrays. The data was then normalized using Robust Multichip Average and an ANOVA analysis was performed to identify genes that are differentially expressed between NOR FC and NOD FC. The 18 most significant differentially expressed genes were selected by false discovery rate (FDR) control analysis with $1.99952^{e-0.05}$ cutoff values, and imported into Ingenuity Pathway Analysis (Ingenuity System) for biological interpretation.

Example 4—Relative Quantitative Real-Time PCR for Dock2

Total RNA was extracted from sorted $1 \times 10^5$ FC using the Arcturus® PicoPure® RNA Isolation Kit (Applied Biosystems) and treated with RQ1 RNase-free DNase (Promega) to eliminate contaminating genomic DNA. The quantification of RNA was measured by NanoDrop (Thermo Scientific) and the quality of RNA templates was assessed by denaturing-formaldehyde agarose gel electrophoresis. 500 ng of total RNA was reverse transcribed into first-strand complementary DNA using iScript™ cDNA Synthesis Kit (Bio-Rad). Real-time qPCR was performed on a CFX96™ Real-Time PCR Detection System (Bio-Rad) with QuantiTect SYBR Green PCR Kit (Qiagen). Pre-designed and bioinformatically validated primers (QT00146342 for Dock2, QT01658692 for Gapdh, QuantiTect Primer Assays, Qiagen) were used to achieve ~100% PCR efficiencies for reliable relative quantification. The results were analyzed with the Bio-Rad CFX Manager™ Software v1.0, normalized to Gapdh gene expression, and compared to the expression of Dock2 in NOR FC using the $2^{-\Delta\Delta Ct}$ Method (Livak et al., 2001, Methods, 25:402-8).

Example 5—Immunofluorescence Staining of DOCK2

$1.5 \times 10^4$ FC sorted were resuspended in 100 µl IMEM medium (Invitrogen) and spun onto Superfrost Plus slides (Thermo Scientific) using a Shandon EZ Cytofunnel and Shandon CytoSpin III Cytocentrifuge (Thermo Scientific). The slides were air dried and fixed in cold acetone for 5 minutes at −20° C. The slides were air dried again, and then washed with PBS for 2 minutes, twice. The cells were blocked with 1% purified casein (Roche Applied Science) in PBS for 1 hour at room temperature, and then incubated with rabbit polyclonal anti-mouse DOCK2 (1:100, Millipore) overnight at 4° C. The slides were washed with PBS for 5 minutes, twice, and then the cells were incubated with Alexa Fluor® 488 goat anti-rabbit IgG (1:400, H+L, highly cross-adsorbed, Invitrogen) for 1 hour at room temperature. After washing with PBS, the cells were subsequently counterstained with DAPI (Invitrogen) for 5 minutes and the slides were mounted in Vectashield medium (Vector).

Example 6—HSC and/or FC Transplantation

For syngeneic transplantation, B6 recipients were conditioned with 950 cGy total body irradiation (TBI) from a Cesium source (Nordion) and transplanted with 500 B6 KSL cells±30,000 B6 WT or DOCK2$^{-/-}$ FC by tail vein injection 6 hours after irradiation. For allogeneic transplantation, B10/BR recipients conditioned with 950 cGy TBI were transplanted with 10,000 B6 KSL cells±30,000 B6 WT or DOCK2$^{-/-}$ FC. Percentage survival reflecting engraftment was followed over time.

Example 7—In Vivo Homing

B6 mice were irradiated with a supralethal dose (1200 cGy) of TBI. After 24 hours, the mice were transplanted with 25,000 B6 KSL cells±75,000 B6 WT or DOCK2$^{-/-}$ FC by tail vein injection. The bone marrow cells were harvested from femurs and tibias of the recipient mice 18 hours after cell injection and were resuspended in 300 µl IMEM medium for colony-forming cell assay.

Example 8—In Vitro Co-Culture of FC and HSC 10,000 B6 KSL cells were incubated alone or in the presence of 45,000 B6 FC or DOCK2$^{-/-}$ FC for 18 hours in long-term culture medium (LTCM) consisting of IMEM medium, 20% horse serum (Invitrogen), $10^{-6}$ mol/L hydrocortisone (Sigma-Aldrich), 50 µM β-mercaptoethanol (Sigma-Aldrich), 50 U/ml penicillin, 50 µg/ml streptomycin (Invitrogen) in a 96-well cell culture cluster (U-bottom with lid, Costar). After co-culture, the cell samples were harvested for apoptosis assay and colony-forming cell assay.

Example 9—Colony-Forming Cell Assay

For the samples from in vivo homing or in vitro FC:HSC co-cultures were collected in 300 µl of IMEM medium, and mixed with 5 ml of methylcellulose medium (MethoCult GF-M3434, Stem Cell Technologies), and were dispensed into four 35-mm dishes (1.1 ml/each dish) using a sterile disposable 1 ml syringe with a 16 gauge blunt end needle (Stem Cell Technologies). After 7 days incubation, enumeration and characterization of colonies were performed blindly by individuals who were not informed about the group information.

Example 10—Apoptosis Assay

Cell samples after the co-culture were re-stained with c-Kit APC and Sca-1 PE antibody for 30 minutes and then incubated with Annexin V-FITC (BD Bioscience) and 7-aminoactinomycin D (7-AAD, Molecular Probes) for 15 min. Cell death and cell apoptosis were determined by staining patterns of Annexin V and 7-AAD in flow cytometry.

Example 11—Generation of Immunosuppressive Treg and Tr1 In Vitro $5 \times 10^5$ WT B6 or B10.BR spleen CD4$^+$CD25$^-$ T cells were incubated with $1 \times 10^5$ WT FC or DOCK2$^{-/-}$ FC at a 5:1 ratio in U bottom 96-well plates for up to 6 days. For intracellular staining for IL-10, cells were stimulated with PMA (20 ng/ml) and ionomycin (1 µg/ml) before harvesting. The co-cultures were harvested and analyzed for generation of immunosuppressive $CD4^+CD25^+Foxp3^+$ Treg and $CD4^+$ $CD25^-IL-10^+$ Tr1 cells from naïve $CD4^+CD25^-$ T cells. WT $CD4^+CD25^-$ splenocytes culture only served as negative control. Phagocytosis of APC-labeled polystyrene beads (BD Biosciences) by WT and $DOCK2^{-/-}$ FC was assessed after incubating FC with the beads for 3 hours.

Example 12—Subpopulation Analysis of $DOCK2^{-/-}$ FC

Sorted FC isolated from bone marrow cells of B6 WT or $DOCK2^{-/-}$ mice were incubated with Fc receptor block before staining with anti-CD3, CD11b, CD11c, B220, NK1.1, DX5, CD14, Gr-1, CD19 (BD Biosciences), PDCA-1 (eBioscience) and CD169 (AbD Serotec). BD LSR II multicolor flow cytometry with FACS Diva™ software (BD Biosciences) were used for the data acquisition and analysis.

Example 13—Transwell Migration Assay

Sorted $1.5 \times 10^5$ FC were resuspended in 300 µl of migration medium (RPMI-1640 medium with 0.5% BSA) and equilibrated for 10 minutes at 37° C., and chemotaxis assays were performed by employing Transwell® 24-well plates (Corning Life Sciences) with 5 µm-pore polycarbonate membrane, 6.5 mm diameter insert. The experimental well was filled with 600 µl of migration medium containing SDF-1 (200 ng/ml) (Millipore) in the lower chamber. The wells with or without the upper insert, but receiving migration medium only in lower chamber, were designated as a passive cell migration control and a cell loading control, respectively. For each group, cell suspension aliquots of 100 µl ($0.5 \times 10^5$ FC) were added to two wells with the upper insert and one well without the insert. After placing the 24-well plate in a 37° C., 5% $CO_2$ incubator for 3 hours, the cells were collected from the lower chamber and the cell number of each well was scored by flow cytometry (FACSCalibur, BD Biosciences) with an adjusted threshold to exclude cell debris. The percentage of cell migration was calculated from the ratio of the absolute number of cells that migrated toward the migration medium containing SDF-1 (after subtracting the number of cells that migrated toward the migration medium alone) to the total number of cells loaded.

Example 14—Cell Tracking of FC

Non-irradiated B6 recipients were transplanted with $1.5 \times 10^5$ B6 WT or $DOCK2^{-/-}$ FC labeled with 2.5 µmol/L CellTracker™ Green CMFDA (Invotrgen). Cell viability and staining efficiencies were checked before the transplantation by trypan blue staining and flow cytometry, respectively. Enumeration of CellTracker™ Green CMFDA labeled FC was performed by flow cytometry in spleen, thymus, and bone marrow of femurs and tibias 18 hours post-transplantation. For bone section observations, irradiated B6 recipients were also used as recipients. The femurs and tibias were harvested and decalcified in 10% EDTA/Tris-HCl (pH 7.4) for 6 days. Decalcified bones were then cryoprotected with optimum cutting temperature (Tissue-Tek), sectioned (10 µm) with a cryostat, mounted onto Superfrost Plus slides (Thermo Scientific). After washing with PBS, the sections were subsequently counterstained with DAPI (Invitrogen) for 5 minutes and the slides were mounted in Vectashield medium (Vector). CellTracker™ Green CMFDA labeled FC were imaged using a Leica TCS SP5 laser confocal microscope and the Leica Application Suite Advanced Fluorescence software.

Example 15—SDF-1 ELISA and Intracellular Staining 150,000 FC from B6 or from $DOCK2^{-/-}$ mice were cultured in LTCM in a 96-well cell culture cluster (V-bottom with lid, Costar) for 48 hours. Cultured FC were fixed and permeabilized with intracellular staining buffer (BioLegend, San Diego, Calif.). SDF-1 APC antibody (R&D Systems, Minneapolis, Minn.) was used to detect SDF-1 positive FC by flow cytometry. Supernatants were collected and ELISA of SDF-1 (R&D Systems, Minneapolis, Minn.) was performed according to the manufacturer's protocol.

Example 16—Statistical Analysis

All results are expressed as mean±SD unless otherwise indicated. Statistical analysis was performed with GraphPad Prism 5 software (GraphPad Software Inc., San Diego Calif.). For two groups, normal distributions were compared by 2-tailed unpaired Student's t test. Non-normal samplings were compared using the Mann-Whitney test. The log-rank test was used for analysis of Kaplan-Meier survival curve. P values of less than 0.05 were considered statistically significant.

Figure 8:
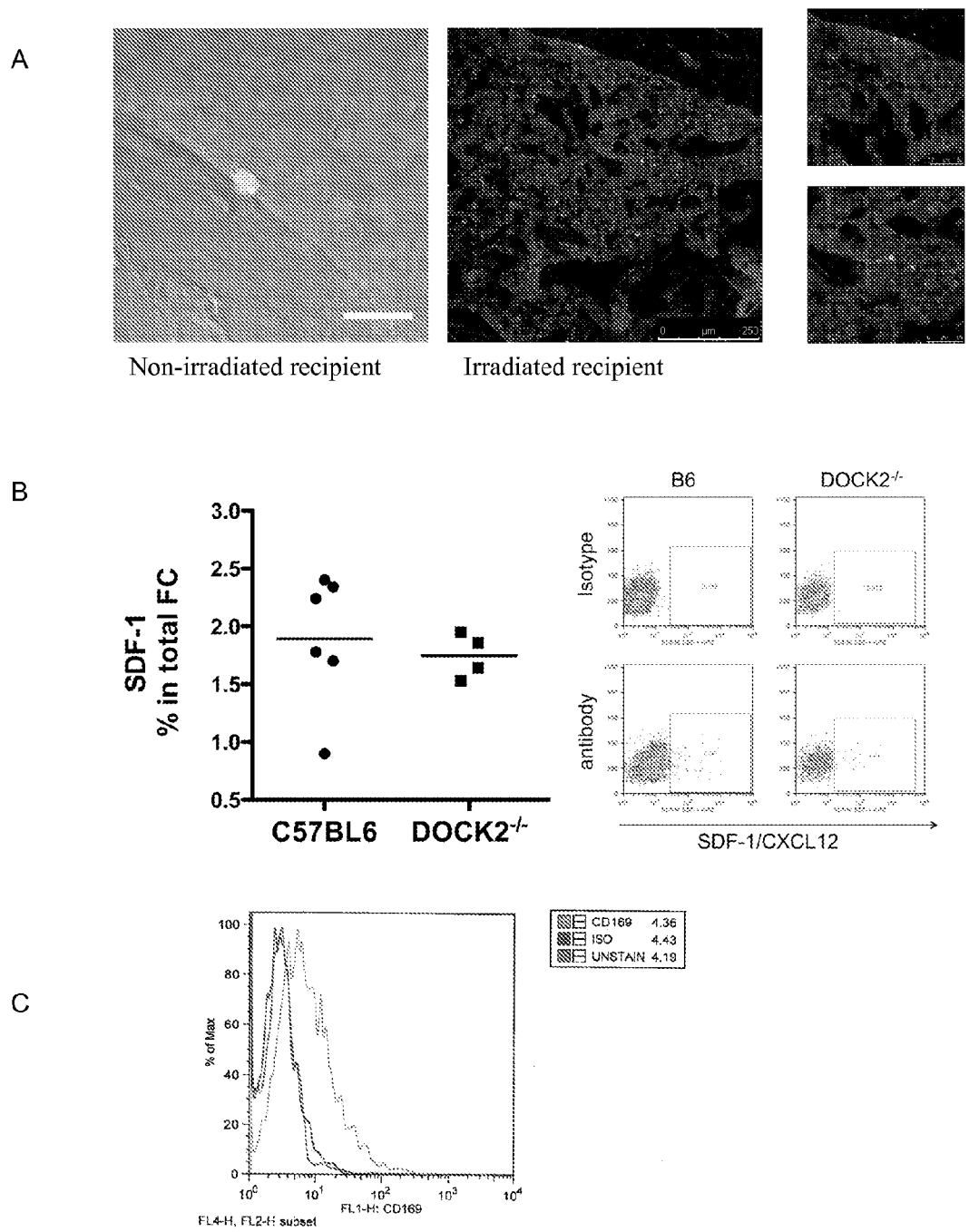
FIG. 8 shows that small fractions of FC sub-populations were CXCL 12-producing cells and CD169$^+$ macrophages. (A) CellTracker Green labeled FC were visualized in frozen bone section of femurs and tibias of both non-irradiated recipients and lethal irradiated recipients. (B) 5% of FC sub-populations were CXCL 12-producing cells and there was no significant difference in CXCL 12$^+$ cells between DOCK2$^{-/-}$ FC and WT B6 FC. (C) There were 3% of FC were 169$^+$ macrophages.

Example 17—Gene Microarray Analysis Revealed DOCK2 Expression was Down-Regulated in FC with Impaired Function A previous study demonstrated that FC from diabetes prone non-obese diabetic (NOD) mice were functionally impaired, while those from congenic normal (NOR) mice were functional (Huang et al., 2008, Diabetes, 57:2360-70). A gene microarray analysis was performed to compare NOD FC to NOR FC. The PCA analysis of the array data showed that three samples within each group were closely clustered together, with a variance of 71.5% of the expression data set, whereas the samples from NOR FC were distinctly separated from NOD FC (FIG. 8), indicating that the quality of the microarray data was excellent in terms of repeatability and the global expression patterns in NOR FC were different from NOD FC. After an ANOVA analysis, a list of 18 genes revealed by FDR control analysis from a total number of 45,101 probe sets was shown in a heat-map (FIG. 1A). Among these 18 genes, dedicator of cytokinesis 2 (DOCK2) was identified as the gene with the most significant difference (NOD FC vs. NOR FC, fold change −21, $p=1.04 \times 10^{-7}$). ARHGAP18 expression was also among the top 18 most significantly different genes (NOD FC vs. NOR FC, fold change +18, $p=7.61 \times 10^{-7}$). Both DOCK2 and ARHGAP18 are found in small GTPase activation pathways known in regulating lymphocyte migration. Scatter plot comparison of mean log 2 expression values of NOR FC versus NOD FC also demonstrated the two genes of interest. DOCK2 expression was shown to be down-regulated and ARHGAP18 was up-regulated (FIG. 1B). These data suggested that the signaling pathways involved in cell migration might be associated with impaired facilitative functions of FC.

Figure 9:
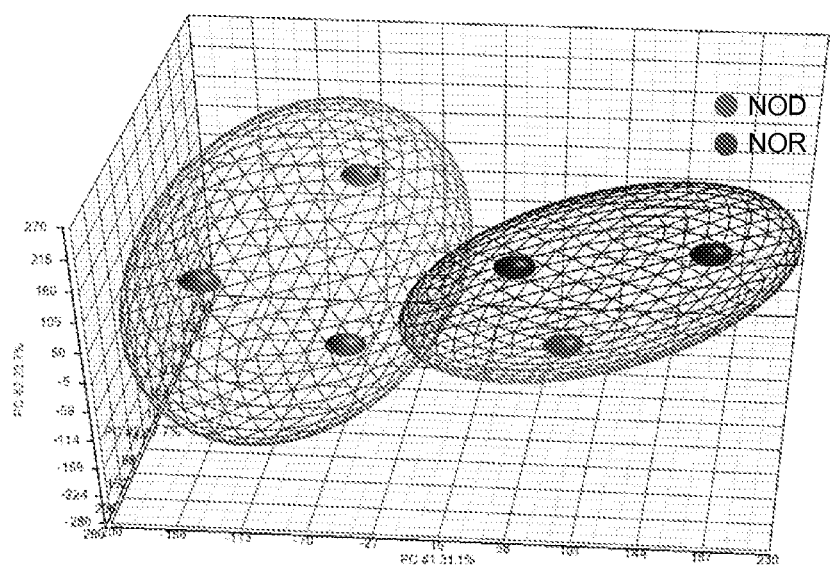
FIG. 9 shows the principle component analysis of microarray results. Each dot represented linear combinations of the expression data of the 45,101 probe sets, including relative expression value and variance. The variance of the expression data set was 71.5%. Each red dot represents one sample of NOD FC, and each blue dot represents NOR FC.

To verify the microarray data of DOCK2 expression, quantitative real-time RT-PCR (qRT-PCR) was performed to compare DOCK2 RNA expression between NOR FC and NOD FC. As suggested by the minimum information for publication of quantitative real-time PCR experiments (MIQE) guidelines (Bustin et al., 2009, Clin. Chem., 611-22), the specificity of SYBR Green based qRT-PCR was validated by melt-curve analysis and agarose gel analysis. There was 1.67 fold decrease in DOCK2 RNA expression in NOD FC compared to NOR FC (FIG. 1C) Immunofluorescence staining of DOCK2 protein was then performed in FCs sorted from individual mice and high content image analysis was run (FIG. 9). It was observed that NOR FC have a higher percent of DOCK2 positive cells than NOD FC in high content image analysis of 2000 cells in FC cytospin samples (FIG. 1D). The data generated from both assays confirmed the observation from the microarray analysis that NOD FC had a significant lack of DOCK2 expression.

Example 18—FC Required DOCK2 to Mediate Facilitation In Vivo

Figure 2:
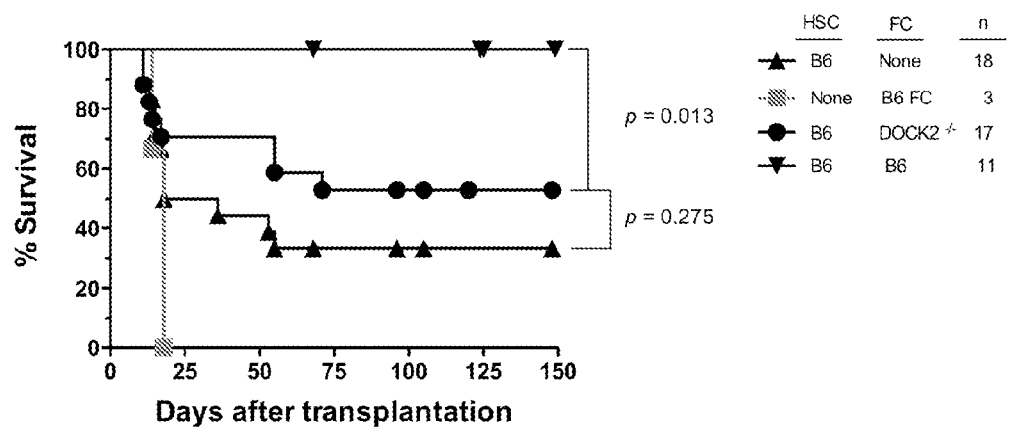
FIG. 2 shows that DOCK2$^{-/-}$ FC are functionally impaired to facilitate HSC engraftment in allogeneic and syngeneic recipients. (A) Syngeneic model: survival of syngeneic B6 recipients transplanted with 500 B6 KSL cells (▲), 30,000 B6 FC alone (■), or 500 KSL cells mixed with 30,000 B6 WT FC (▼) or DOCK2$^{-/-}$ FC (●). (B) Allogeneic model: survival of allogeneic B10.BR (H-2$^k$) recipients transplanted with 10,000 B6 (H-2$^b$) KSL cells (▲), 30,000 B6 WT FC alone (■) or 10,000 B6 KSL cells mixed with 30,000 B6 FC (▼) or DOCK 2$^{-/-}$ FC (●).
Figure 2:
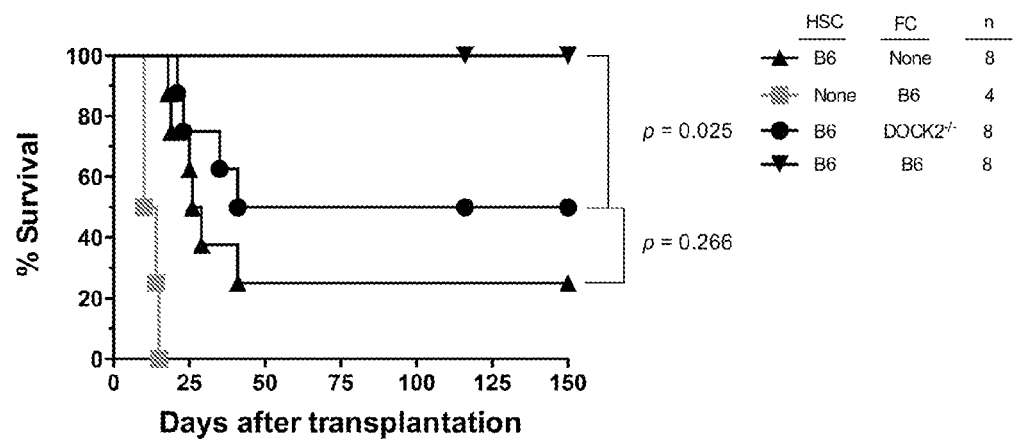

Both syngeneic and allogeneic models for FC function were utilized to determine whether DOCK2 is critical to FC function in vivo. In the syngeneic model (Grimes et al., 2004, Exp. Hematol., 32:946-54), where HSC numbers are limiting, it was found that DOCK2 was critical to FC function. 500 B6 KSL cells were sorted and transplanted alone, or with B6 WT FC, or with DOCK2$^{-/-}$ FC into ablated B6 recipients. Administration of DOCK2$^{-/-}$ FC with HSC resulted in significantly impaired outcomes compared to WT B6 FC (FIG. 2A). Similarly, FC function was significantly compromised when DOCK2$^{-/-}$ FC were tested in the allogeneic model (FIG. 2B). As expected, FC themselves did not exhibit repopulating capability in either model (FIGS. 2A and 2B). For both models, outcomes with DOCK2$^{-/-}$ FC plus HSC were not significantly different from HSC alone (FIGS. 2A and 2B). Taken together, these data demonstrate a critical role for DOCK2 in FC function.

Figure 3:
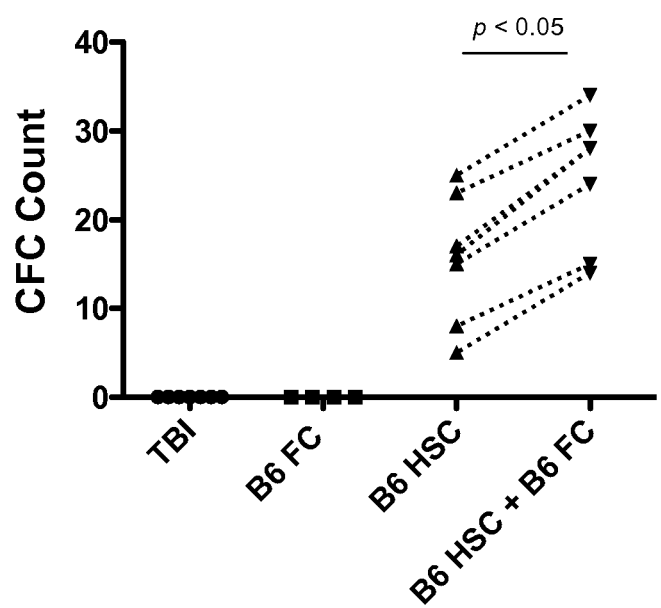
FIG. 3 shows that DOCK2$^{-/-}$ FC are unable to enhance HSC homing and retention in the bone marrow environment. B6 mice were irradiated with a superlethal dose (1200 cGy) of TBI. At 24 hours after irradiation, the mice were transplanted with 75,000 B6 FC alone; 25,000 B6 KSL cells alone; or 25,000 B6 KSL cells with 75,000 B6 WT FC or with 75,000 DOCK2$^{-/-}$ FC. Numbers of the colonies formed from bone marrow cells from femurs and tibias of recipient mice at 18 hours post transplantation were evaluated by performing colony-forming cell assay after in vivo homing. (A) There were significantly more colonies in HSC plus FC group in comparison with the HSC alone group. The mice transplanted with FC alone and the mice treated with irradiation alone were used as controls. The samples from the same experiments are linked by dashed lines. (B) FC augmentation of HSC colony formation after in vivo syngeneic homing was abrogated in the cell migration-compromised DOCK 2$^{-/-}$ FC plus HSC group compared to wild-type FC plus HSC group.
Figure 3:
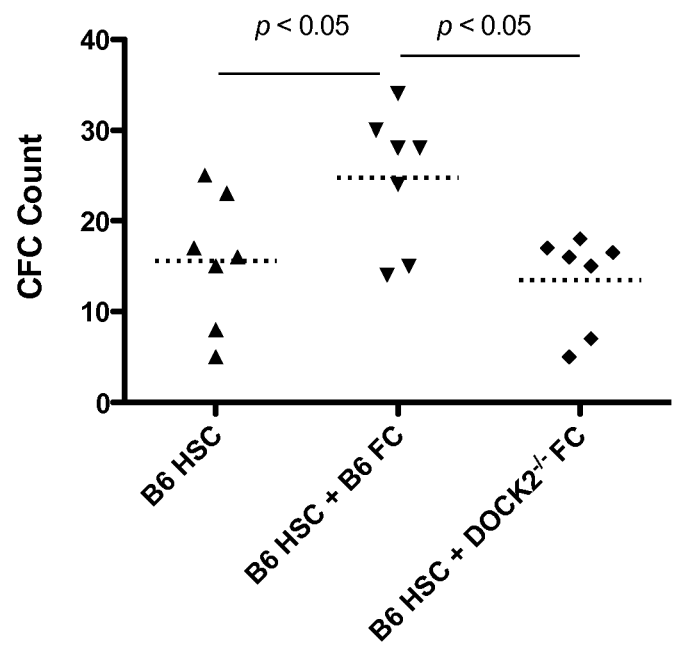

Example 19—DOCK2$^{-/-}$ FC were Significantly Compromised in their Ability to Enhance HSC Homing and Lodgment Homing and lodgment of HSC within the bone marrow niche is believed to be a crucial prerequisite for engraftment. It was therefore evaluated whether DOCK2$^{-/-}$ FC failed to augment HSC homing and retention by using the in vivo syngeneic homing model followed by CFC assay. Bone marrow cells harvested from mice transplanted with FC alone or conditioning alone did not generate colonies. These data confirmed that there was no recipient's HSC left after the supralethal dose of TBI, and FC themselves did not have repopulation capacity in vivo. Notably, the bone marrow cells harvested from mice transplanted with HSC and FC formed significantly higher numbers of colonies compared to that from mice transplanted with HSC alone (FIG. 3A). Compared with mice transplanted with B6 WT FC and HSC, however, colony formation reflecting functional donor HSC retention within recipient bone marrow was significantly reduced when DOCK2$^{-/-}$ FC were co-transplanted with HSC (FIG. 3B), which suggests that DOCK2$^{-/-}$ FC were unable to enhance HSC homing and lodgment within bone marrow microenvironment.

Example 20—DOCK2$^{-/-}$ FC Had Similar Subpopulation Profiles as WT B6 FC

Figure 4:
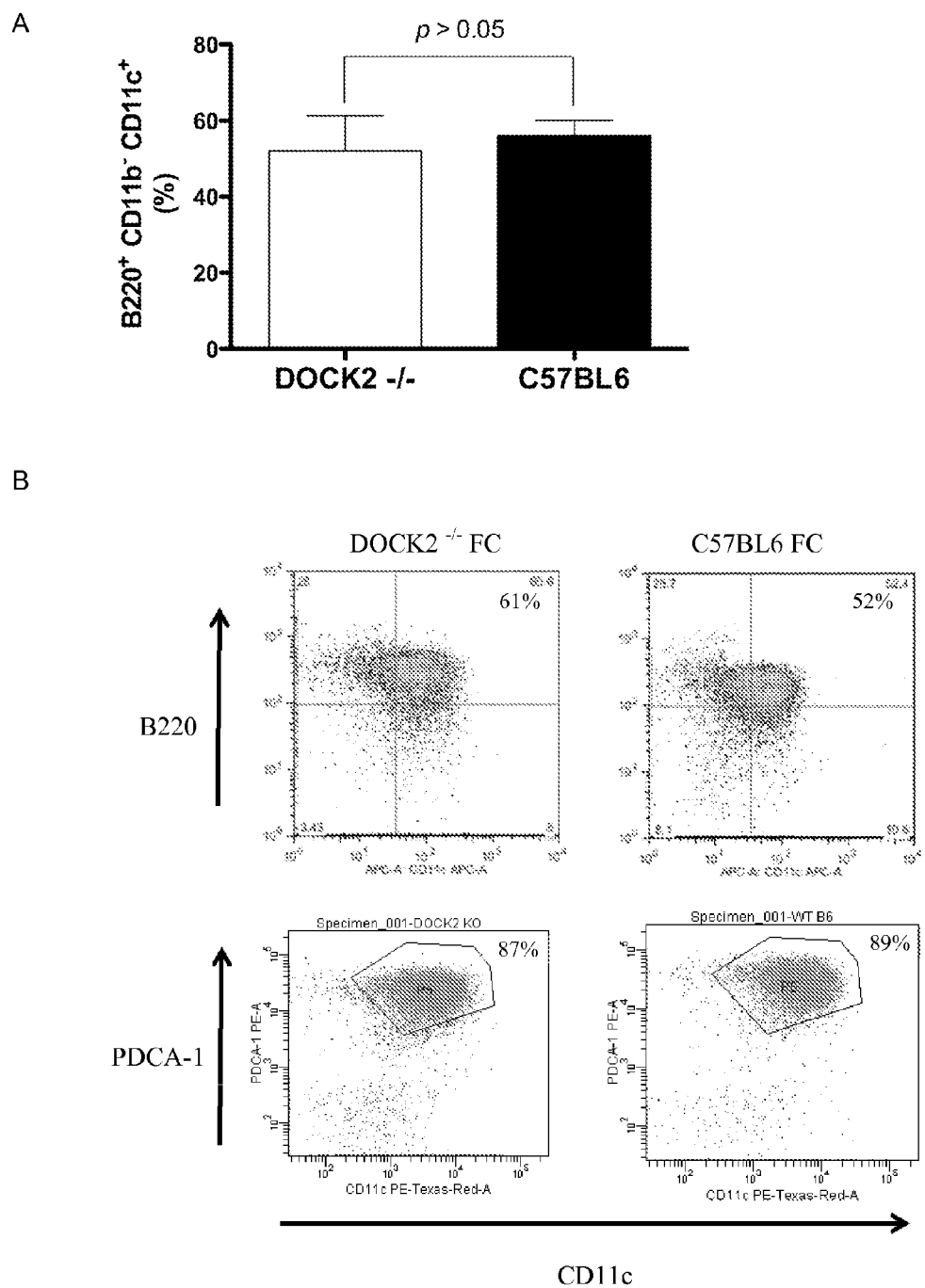
FIG. 4 shows that DOCK2$^{-/-}$ and wild type (WT) genotypes contained a similar fraction of plasmacytoid precursor dendritic cells. (A) Percentage of P-preDC (B220$^+$/CD11c$^+$/CD11b$^-$) FC in CD8$^+$TCRαβ$^-$TCRγδ$^-$ total FC population. (B) Representative FACS profiles of P-preDC gated on B220$^+$/CD11c$^-$/CD11b$^-$ or PDCA-1$^+$/CD11c$^{int}$/CD 11b$^-$ from CD8$^+$TCRαβ$^-$/TCRγδ$^-$ total FC population.

To address the possibility that the impaired function of DOCK2$^{-/-}$ FC was not due to the difference in FC subpopulation profiles, it was determined the subpopulation previously characterized as FC (Fugier-Vivier et al., 2005, J. Exp. Med., 201:373-83; Kaufman et al., 1994, Blood, 84:2436-46). There was no significant difference in subpopulation profiles (P-preDC B220$^+$/CD11c$^+$/CD11b$^-$ or PDCA-1$^+$/CD11c$^{int}$/CD11b$^-$) between DOCK2$^{-/-}$ FC and WT FC (FIG. 4).

Figure 5:
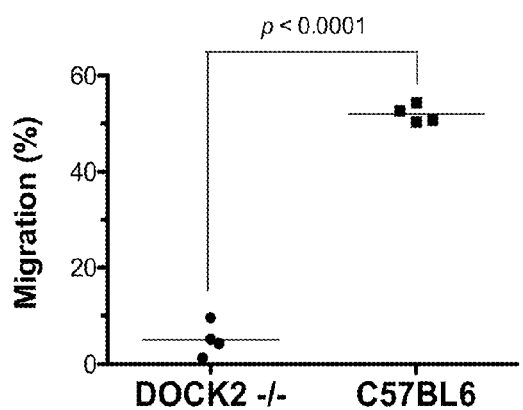
FIG. 5 shows that DOCK2$^{-/-}$ FC exhibited compromised migration to the chemokine CXCL12 in vitro and impaired homing to the bone marrow microenvironment in vivo. Migration function of DOCK2-deficient FC was determined by Transwell migration assay and enumeration of CellTracker Green labeled FC by flow cytometry in spleen, thymus, and bone marrow of femurs and tibias 18 hours post-transplantation. (A) DOCK2$^{-/-}$ FC were compromised in migration to the α-chemokine, stromal derived factor-1 (SDF-1) at the dose of 200 ng/ml. (B) Homing of FC to bone marrow of femurs and tibias was also significantly impaired in DOCK2-deficient FC. Representative flow cytometry plots of CellTracker Green labeled FC in bone marrow of femurs and tibias.
Figure 5:
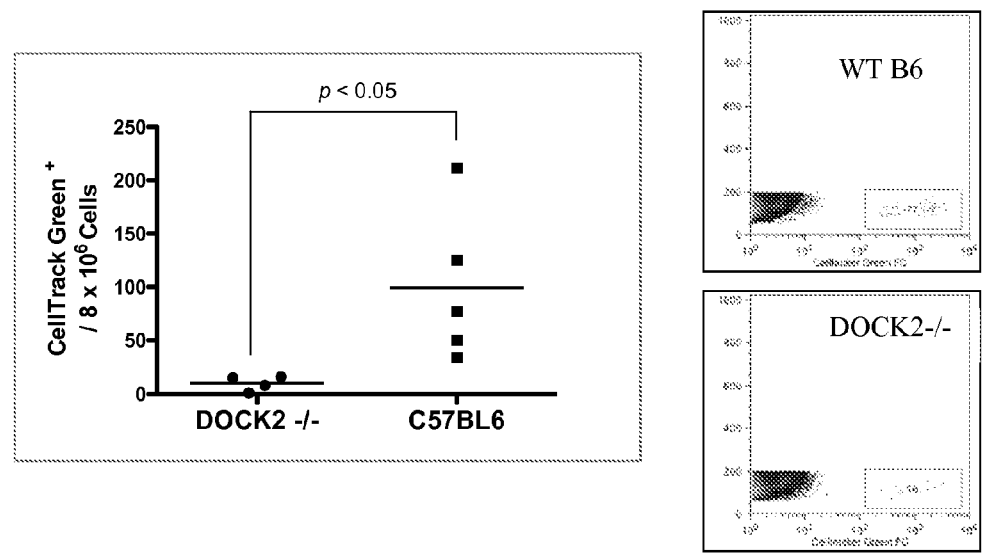
Figure 10:
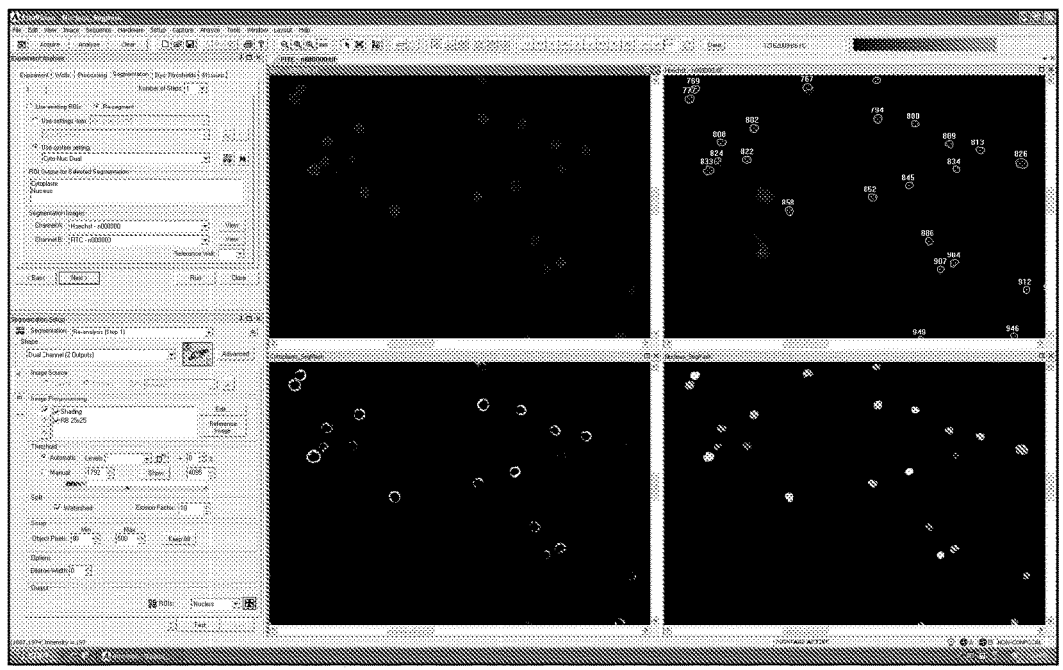
FIG. 10 shows an image analysis for DOCK2 expression. Fluorescence was imaged with a BD Pathway™ 855 Bioimager (BD Bioscience) to generate a montage image of 2000 cells and the image was analyzed by BD Attovision™ Software v1.7 with a segmentation setting of dual channel and two outputs (nucleus and cytoplasm). Images recorded from two controls (cells only and second antibody incubation alone) were used to set up the threshold level for imaging processing.

Example 21—DOCK2$^{-/-}$ FC Exhibit Compromised Migration to SDF-1 In Vitro and Impaired Homing to the Bone Marrow Microenvironment In Vivo The chemokine receptor CXCR4 plays a pivotal role in HSC homing. It was then determined whether the effect of FC on HSC homing was mediated by FC increasing CXCR4 expression in HSC. CXCR4 expression in HSC was measured by flow cytometry 18 hours after co-culture of HSC and FC in vitro. Incubation of FC with HSC did not lead to any alteration of CXCR4 expression in HSC compared with HSC cultured alone (FIG. 10). Previous studies suggested that cell:cell interactions between FC and HSC was necessary for FC facilitation. It was thus investigated whether DOCK2$^{-/-}$ FC was compromised in migration. Chemotaxis of DOCK2$^{-/-}$ FC were determined by Transwell migration assay and CellTracker Green labeled FC were enumerated by flow cytometry in spleen, thymus, and bone marrow of femurs and tibias 18 hours post-transplantation of FC to non-irradiated B6 recipients. DOCK2$^{-/-}$ FC were significantly compromised in migration to the α-chemokine, stromal derived factor-1 (SDF-1, CXCL12) at a dose of 200 ng/ml (FIG. 5A). There was no CellTracker Green labeled FC detected in thymus. Numbers of DOCK2$^{-/-}$ FC homing to spleen were comparable to WT B6 FC. However, FC homing to bone marrow of femurs and tibias was significantly impaired in DOCK2$^{-/-}$ FC (FIG. 5B).

Figure 6:
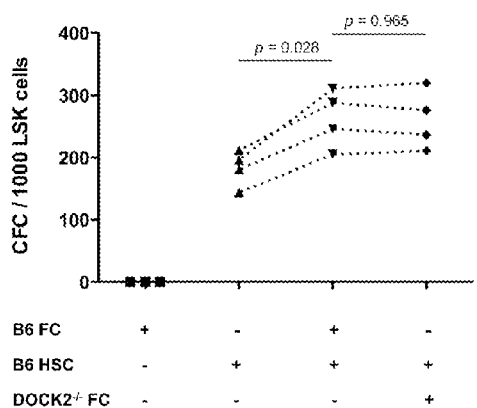
FIG. 6 shows the tropic effects of DOCK2$^{-/-}$ FC on HSC in vitro. (A) DOCK2$^{-/-}$ FC possessed the ability to foster HSC to generate colonies as WT FC did if FC were pre-co-cultured with HSC. Representative colonies (CFU-GM, CFU-M) generated from both groups were shown at right side. (B) DOCK2–/– FC were unable to prevent HSC apoptosis when co-cultured with HSC. Bone marrow CD8+ T cells plus HSC was used as control. Representative FACS profiles of 7-AAD$^-$/Annexin V$^-$ living cells gated from c-Kit+/Sca-1+ population after co-culture FC with HSC.
Figure 6:
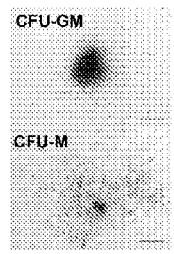
Figure 6:
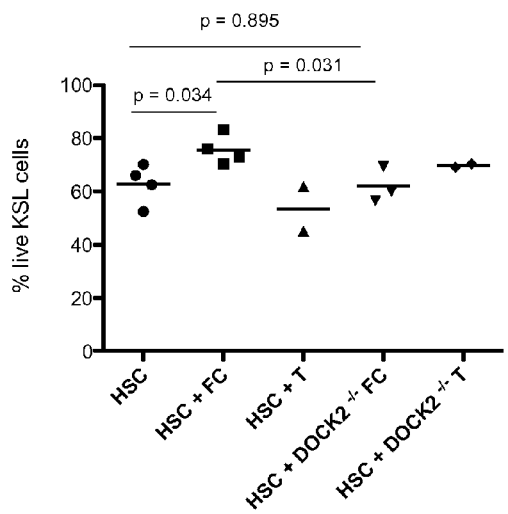
Figure 6:
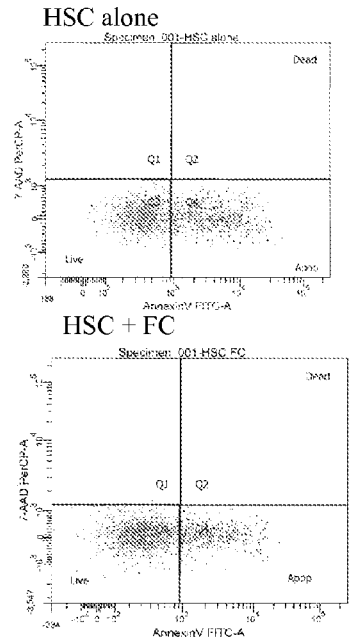

Example 22—DOCK2$^{-/-}$ FC were Able to Promote HSC Colony Formation, but Unable to Prevent HSC Apoptosis In Vitro It was then tested whether the deficiency of DOCK2 in FC affected the ability of FC to promote HSC colony formation and prevent HSC apoptosis in vitro. There was no significant difference in colony formation between DOCK2$^{-/-}$ FC and WT B6 FC when FC were mixed with HSC directly and homing of FC was not required (FIG. 6A). However, DOCK2-/- FC were compromised in preventing HSC apoptosis when co-cultured with HSC (FIG. 6B).

Example 23—DOCK2$^{-/-}$ FC Completely Lost the Ability to Induce Treg and Tr1 Cells In Vitro It was previously found that FC induced antigen-specific T regulatory cells (T$_{reg}$) in vitro and in vivo. A recent study demonstrated that DOCK2$^{-/-}$ DC were defective in antigen uptake and presentation. Therefore, it was evaluated whether DOCK2$^{-/-}$ FC could induce T$_{reg\,and}$ Tr1 immunosuppressive cells. WT FC induced the generation of CD4$^+$CD25$^+$FoxP3$^+$ T$_{reg}$ and IL-10 producing Tr1 cells in vitro as expected, while the DOCK2 deficiency completely abrogated the ability of FC to induce generation of T$_{reg}$ and Tr1 cells (FIG.

Figure 7:
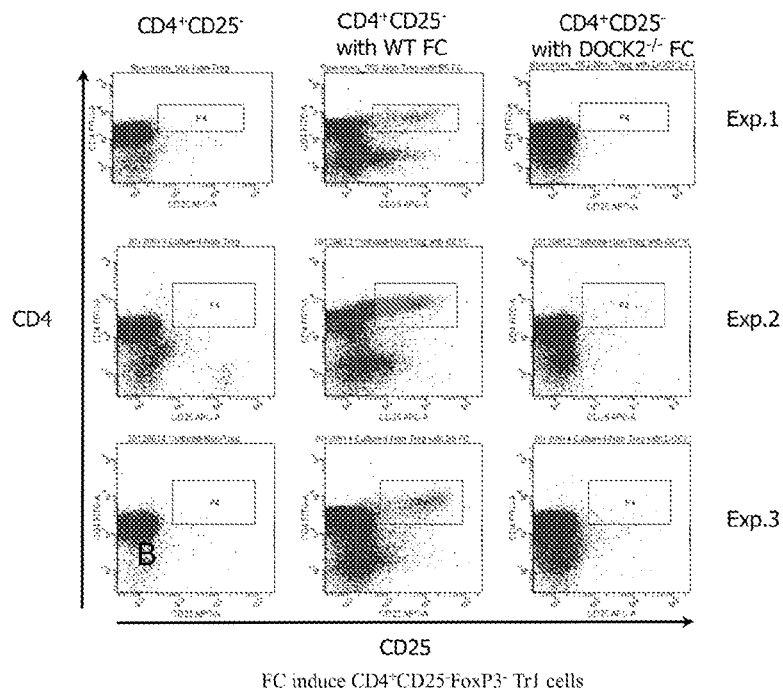
FIG. 7 shows the generation of immunosuppressive T regulatory cells (Treg) and IL-10 producing Tr1 cells. (A) Representative staining for CD4$^+$CD25$^+$ after co-culture. (B) Representative staining for intracellular IL-10 gated on CD4$^+$CD25$^-$ T cells. (C) The uptake of beads by DOCK2$^{-/-}$ FC was significantly impaired compared to their uptake by WT FC. The result is representative of three independent experiments.
Figure 7:
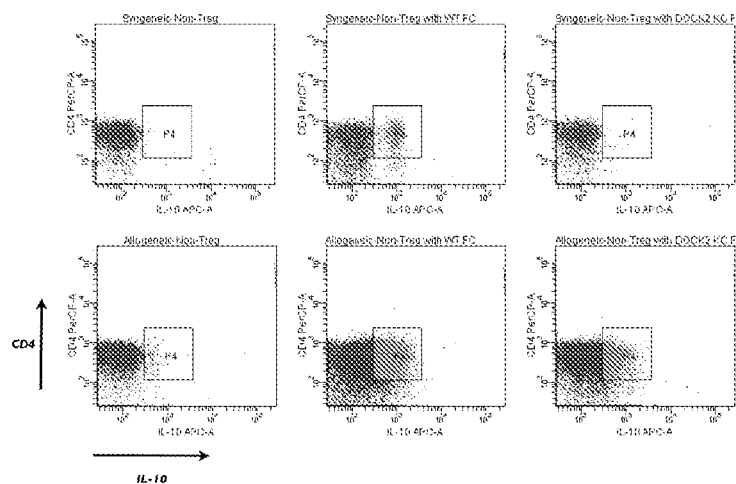
Figure 7:
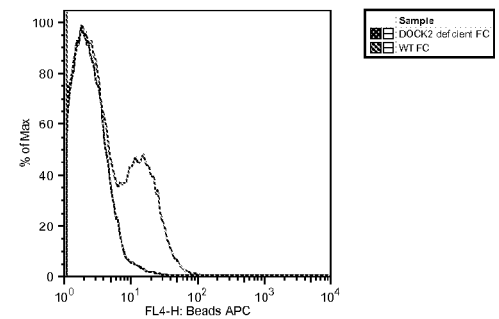

7A, B). Moreover, the uptake of beads by DOCK2$^{-/-}$ FC was significantly impaired compared to their uptake by WT FC (FIG. 7C).

Figure 11:
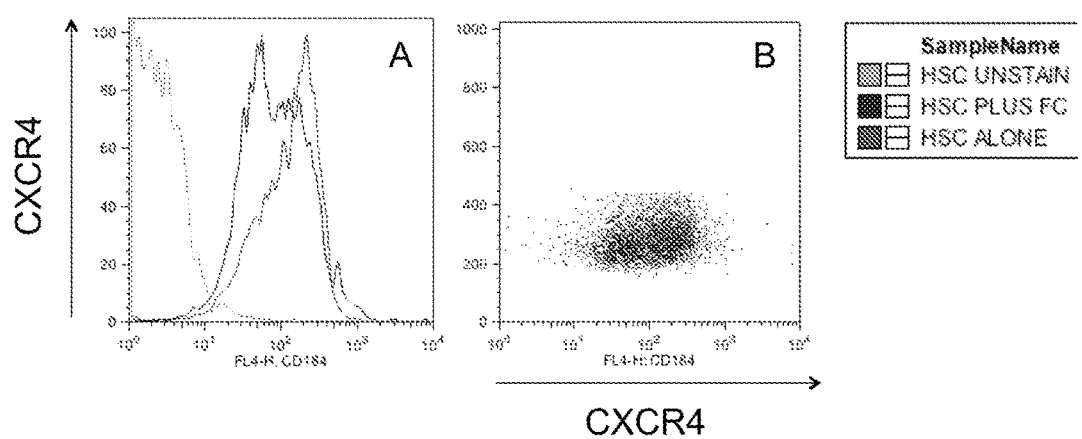
FIG. 11 shows that incubation of FC with HSC did not lead to any alteration of CXCR4 expression in HSC compared with HSC cultured alone. CXCR4 expression in HSC was measured by flow cytometry 18 hours after co-culture of HSC and FC in vitro. (A) HSC unstaining control (green line); HSC alone (blue line); and HSC co-cultured with FC (red line). (B) Overlay of CXCR4-positive cells. HSC alone (blue dots); and HSC co-cultured with FC (red dots).
Figure 12:
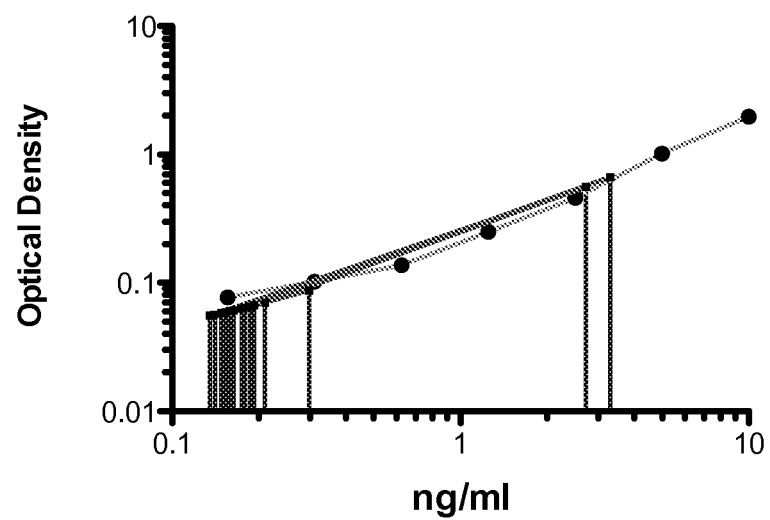
FIG. 12 shows that.SDF-1 is present in supernatant of FC culture. Low concentration (0.2 ng/ml) of SDF-1 was also detected in 100 μl supernatants of cultured FC.

Example 24—Small Fractions of FC Sub-Populations were CXCL 12-Producing Cells and CD169$^+$ Macrophages FC homing to the bone marrow niche was confirmed by identifying CellTracker Green labeled FC in frozen bone section of femurs and tibias of both non-irradiated recipients and lethal irradiated recipients (FIG. 8A). These data suggested homing to the bone marrow niche might be a prerequisite for FC functions. CXCL 12 (SDF-1)-abundant reticular (CAR) cells, perivascular mesenchymal cells (Nestin$^+$) and bone marrow CD169$^+$ macrophages are putative components of the HSC perivascular niche. There were 5% FC positive for SDF-1 and no significant difference between DOCK2$^{-/-}$ FC and WT B6 FC (FIG. 8B). Low concentration (0.2 ng/ml) of SDF-1 was also detected in 100 µl supernatants of cultured FC (FIG. 11). In addition, it was found that 3% of FC were 169$^+$ macrophages (FIG. 8C).

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. A method of enhancing the function of CD8+/TCR– facilitating cells, comprising the step of:
    contacting said facilitating cells (FCs) ex vivo with exogenous DOCK2 polypeptides.
2. The method of claim 1, wherein the DOCK2 polypeptides are human DOCK2 polypeptides.
3. The method of claim 1, wherein the DOCK2 polypeptides are recombinant DOCK2 fusion polypeptides.
4. The method of claim 1, wherein the FCs are purified.
5. The method of claim 1, wherein the function of the FCs comprises in vitro migration to SDF-1, in vitro induction of T regulatory cells (Treg), in vitro induction of Tr1 cells, enhancing hematopoietic stem cell (HSC) homing, enhancing HSC lodgment, or preventing HSC apoptosis.
6. The method of claim 5, wherein the ability of the FCs to enhance HSC homing and/or enhance HSC lodgment is determined using an in vivo syngeneic homing model followed by a CFC assay.

* * * * *